United States Patent [19]

Buechel et al.

[11] Patent Number: 4,752,296

[45] Date of Patent: Jun. 21, 1988

[54] PROSTHESIS WITH INTERLOCKING FIXATION AND PROVIDING REDUCTION OF STRESS SHIELDING

[76] Inventors: Frederick F. Buechel, 76 Crest Dr., South Orange, N.J. 07079; Michael J. Pappas, 61 Gould Pl., Caldwell, N.J. 07006

[21] Appl. No.: 830,208

[22] Filed: Feb. 18, 1986

Related U.S. Application Data

[63] Continuation-in-part of Ser. No. 492,131, May 6, 1983, abandoned.

[51] Int. Cl.⁴ ............................................. A61F 2/36
[52] U.S. Cl. ........................................ 623/23; 623/18
[58] Field of Search ............................ 623/16–23; 128/92

[56] References Cited

U.S. PATENT DOCUMENTS 3,840,904 10/1974 Tronzo ................................. 623/23
4,328,593 5/1982 Sutter et al. ......................... 623/22

FOREIGN PATENT DOCUMENTS 2845231 5/1979 Fed. Rep. of Germany ........ 623/22
2838335 3/1980 Fed. Rep. of Germany ........ 623/23
995762 12/1951 France ................................. 623/23

OTHER PUBLICATIONS

Judet, "Stainless Steel Femoral Prosthesis", Journal of Bone & Joint Surgery, Feb. 1954, vol. 36-B, #1, p. 13.

Primary Examiner—Richard J. Apley
Assistant Examiner—David J. Isabella
Attorney, Agent, or Firm—Anthony J. Casella; Gerald E. Hespos

[57] ABSTRACT

A prosthesis including a load receiving surface for receiving a load applied to the prosthesis, a first surface provided with interlocking means for interlocking fixation of a first bone portion and for transferring a portion of the applied load to the first bone portion, and a second surface which is smooth to cause an increase in the portion of the applied load applied to the first bone portion to increase the stress produced therein thereby substantially reducing stress shielding in the first bone portion and resorption of bone therein.

3 Claims, 6 Drawing Sheets

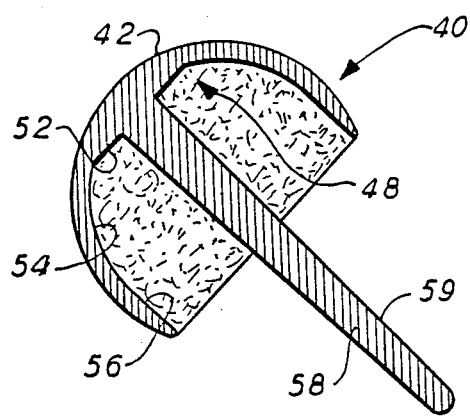
FIG. 3A
FIG. 3B
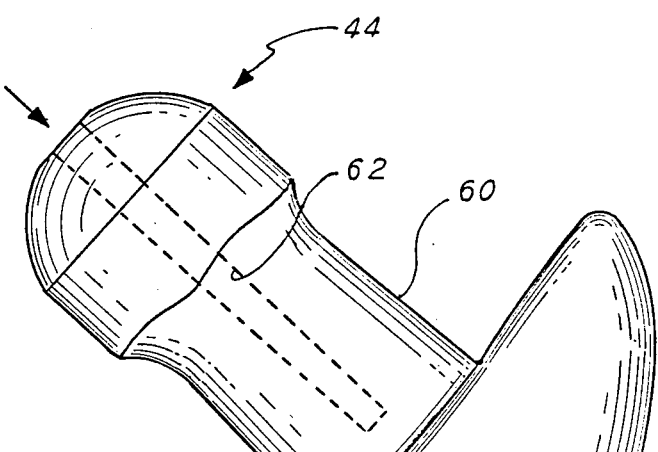
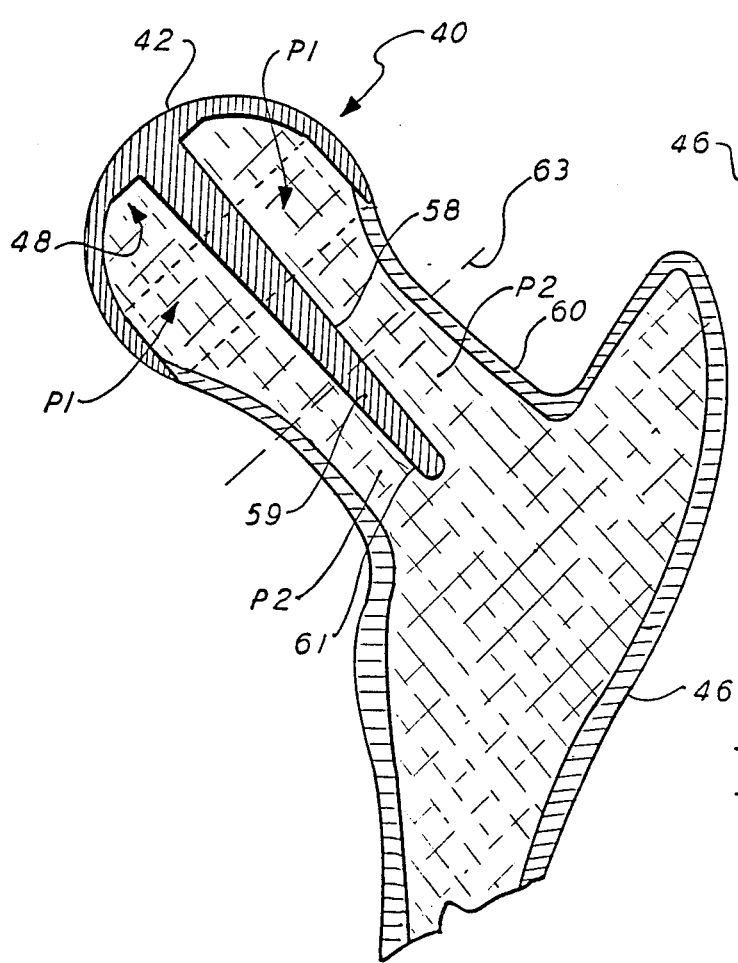
FIG. 3C

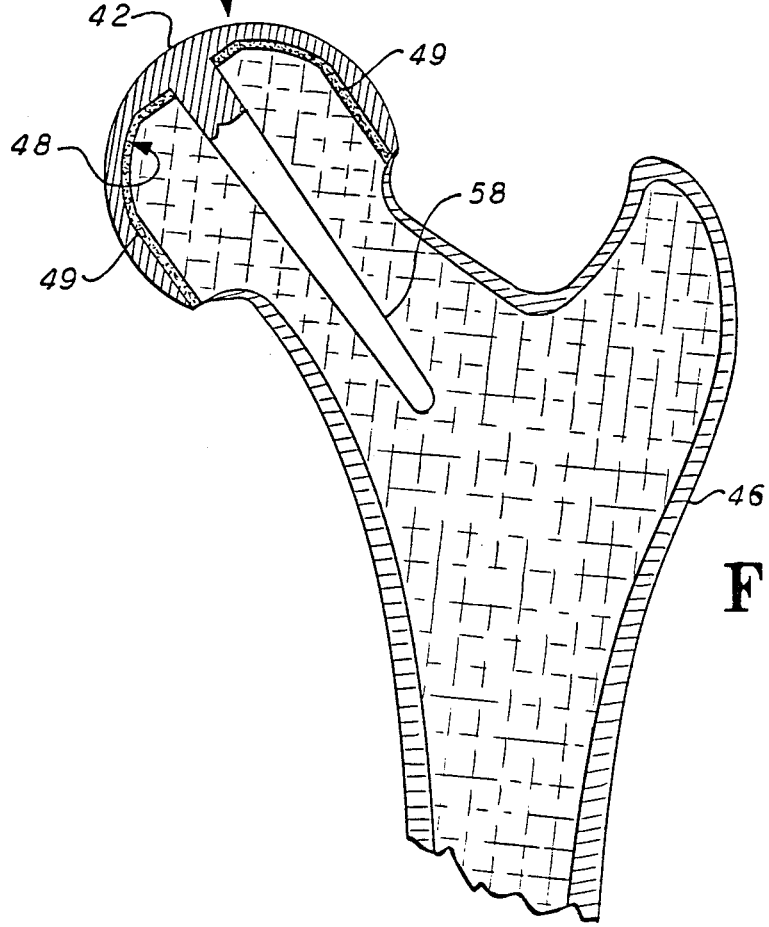

PROSTHESIS WITH INTERLOCKING FIXATION AND PROVIDING REDUCTION OF STRESS SHIELDING

CROSS-REFERENCE TO RELATED APPLICATIONS

This application is a continuation-in-part of pending patent application Ser. No. 492,131 filed May 6, 1983 now abandoned, for PROSTHESIS WITH INTERLOCKING FIXATION AND PROVIDING REDUCTION OF STRESS SHIELDING in the names of Frederick F. Buechel and Michael J. Pappas.

BACKGROUND OF THE INVENTION

This invention relates generally to a partially porous coated prosthesis with interlocking fixation and the provision of stress shielding reduction.

Prosthesis fixation by growth of bone into porous-coated implants is well known in the art as an alternative fixation means to the use and known limitations of various other fixation means, for example screws, spikes, acrylic cement, etc. As is further known in the art with regard to such porous-coated implants, bone has been shown to grow into the voids of porous coated prostheses producing a mechanically effective biological bond. The interlocking of viable bone with the porous prosthetic surface has been found to provide a three-dimensional fixation which resists both tensile and shear stress at the implant-bone interface.

A porous coating can also be employed to improve the bonding ability of bone cement. Where cement is used in apposition to a smooth prosthetic surface, as is often the case, one obtains a relatively weak bond at the prosthesis-cement interface. Properly applied bone cement, however, produces a strong cement to bone interface wherein the cement is forced into the interstices of the bone. The strength of fixation is limited by the strength of the relatively weak prosthesis to cement interface and does not utilize effectively the strength of the bone to cement interface. The use of a porous surface prosthesis, however, produces interlocking at both the cement-bone and prosthesis-cement interfaces thus producing three-dimensional fixation which is resistant to both tensile and shearing loads.

Stress shielding is a problem that is also known in the porous-coated implant art which stress-shielding is taught in detail in an article entitled, "POROUS INGROWTH FIXATION OF THE FEMORAL COMPONENT IN A CANINE SURFACE REPLACEMENT OF THE HIP," by Anthony K. Hedley et al., published March 1982, No. 163, Clinical Orthopaedics & Related Research. As taught in detail in the Hedley et al. article, and as shown diagrammatically in FIG. 1 of the drawings, which FIG. is taken from FIG. 4 of the Hedley article, it is known and illustrated that upon the entire interior surface 12 of a femoral hip surface replacement component 10 being porous-coated, and upon the prosthesis being implanted in the head of the femur 14, bone ingrowth will occur at the interface between the bone and the porous coated prosthesis stem 16 providing good fixation but it has been found, as illustrated, that the load or stress will be transferred to this interface, and the interface between the head of the femur and the interior surface 12 of the prosthesis will be shielded from the load or stress which is transferred to the interface between the bone and the porous coated stem 16 and this stress-shielding has been found to cause resorption and hypertrophy at the head of the bone causing the shown void between the head of the femur 14 and the interior surface 12 of the prosthesis 10. As is further known to those skilled in the art, interior wall fixation and bone ingrowth between the head of the femur 14 and the interior surface 12 of the prosthesis 10 is more desirable than fixation and bone ingrowth between the femur 14 and porous-coated surface of the stem 16 because it provides a more uniform loading between the prosthesis and the femur and a more uniform transfer of stress from the prosthesis to the resected femoral head. As is also taught in the Hedley et al. article, in FIG. 6 thereof, and as shown in FIG. 2 of the drawings taken from such FIG. 6, the stress-shielding problem associated with the porous coating of the surface of the stem 16 of the prosthesis 10 of FIG. 1 can be eliminated by eliminating the stem thereby producing direct bone ingrowth between the resected head of the femur 14 and the entire interior surface 12 of the prosthesis 10 achieving the above-noted preferable fixation between the bone and the interior wall of the prosthesis with its attendant uniform loading and stress transfer.

Although the use of a stem is not necessary for the purpose of providing axial fixation in a bone capping type prosthesis as described in Hedley, in other applications a stem is important in providing initial fixation in order to provide fixation means while bone ingrowth occurs in order to minimize patient or joint immobilization for an undesirably lengthy period of time or to help prevent motion between the bone and prosthesis interfaces which can occur as a result of patient movement wherein such motion can prevent ingrowth by repeated rupture of early bone ingrowth with resultant fixation failure.

The use of stems also can provide alignment capabilities improving the positional accuracy of placement of the prosthesis. Further, stems can provide fixation which augments resistance to the joint reaction loads and can be useful in preventing possible fractures.

Stress shielding can also occur with cemented prostheses where the cement provides the strong interlocking between implant and bone. This phenomenon has been seen clinically on well fixtured hip stem prostheses in cases where there is excellent distal fixation of the stem. This situation produces load transfer from prosthesis to bone at the distal aspect of the prosthesis leaving the bone proximal to this region unloaded thereby resulting in stress shielding and resorption of the proximal bone.

The auxiliary stem functions, including alignment, initial fixation fracture prevention, and load augmentation can all be considered as providing secondary fixation since all provide at some time a load transfer function. The alignment function provides load transfer between prosthesis and bone during implantation wherein this loading controls positioning of the component during implantation. Preventing of fracture also involves load transfer preventing overloading of predetermined regions of bone.

For a prosthesis made of material, such as metal or ceramic, substantially stiffer than bone, and where firm fixation and substantial load transfer occurs in bony regions remote from the load application surface, loading of the bony regions nearer the load application surface is substantially reduced shielding the nearer bone against stress. On the other hand, if firm fixation and substantial load transfer occurs in bony regions near the load application surface, loading of bone further from the load application surface is not substantially reduced and therefore such bone is not substantially protected against stress. Thus, for relatively stiff prostheses it is desirable to design fixation so as to minimize load transfer regions of bone away from the load application surface in order to minimize bone resorption of bone nearer the load application surface.

Accordingly, it is a primary object of the present invention to provide an improved prosthesis providing interlocking fixation between the prosthesis and a bone and reducing the above-noted stress shielding problem.

SUMMARY OF THE INVENTION

The present invention overcomes the above-noted stress shielding problem by providing a prosthesis including a load receiving surface for receiving a load applied to the prosthesis, a first surface provided with interlocking means for interlocking fixation of a first bone portion and for transferring a portion of the applied load to the first bone portion, and a second surface which is smooth to cause an increase; in the portion of the applied load applied to the first bone portion to increase the stress produced therein thereby substantially reducing stress shielding in the first bone portion and resorption of bone therein.

A surface is said to be smooth in the context of the present invention if the strength of the bond obtainable between such a surface and material adjacent to it is substantially less than that obtainable between an interlocking surface and a similar adjacent material.

In a preferred embodiment of the present invention, the first surface is a porous coating for either direct bone ingrowth interlocking fixation or for engaging cement for securing the prosthesis to the bone.

DESCRIPTION OF THE DRAWINGS

FIGS. 3A, 3B, and 3C are diagrammatical illustrations of a femoral hip surface replacement prosthesis embodying the present invention, with the prosthesis of FIGS. 3A and 3C shown in cross-section;

FIGS. 4A and 4B show a humeral surface replacement prosthesis embodying the present invention, with FIG. 4B being a cross-sectional view taken substantially along the plane B—B in the direction of the arrows in FIG. 4A;

FIG. 6 is a view, in partial cross-section, of a humeral stem prosthesis embodying the present invention;

FIG. 8 is a femoral surface replacement prosthesis, similar to the one illustrated in FIG. 3A, but showing the prosthesis used in conjunction with cement.

DESCRIPTION OF THE PREFERRED EMBODIMENTS

Figure 1:
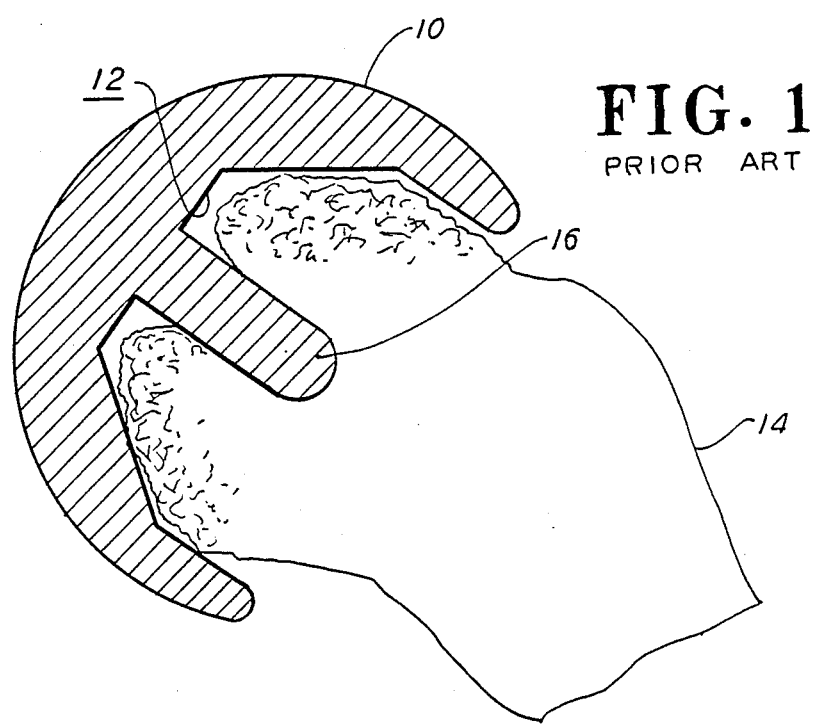
FIGS. 1 and 2 are diagrammatical illustrations of stress shielding from the prior art as noted above.
Figure 2:
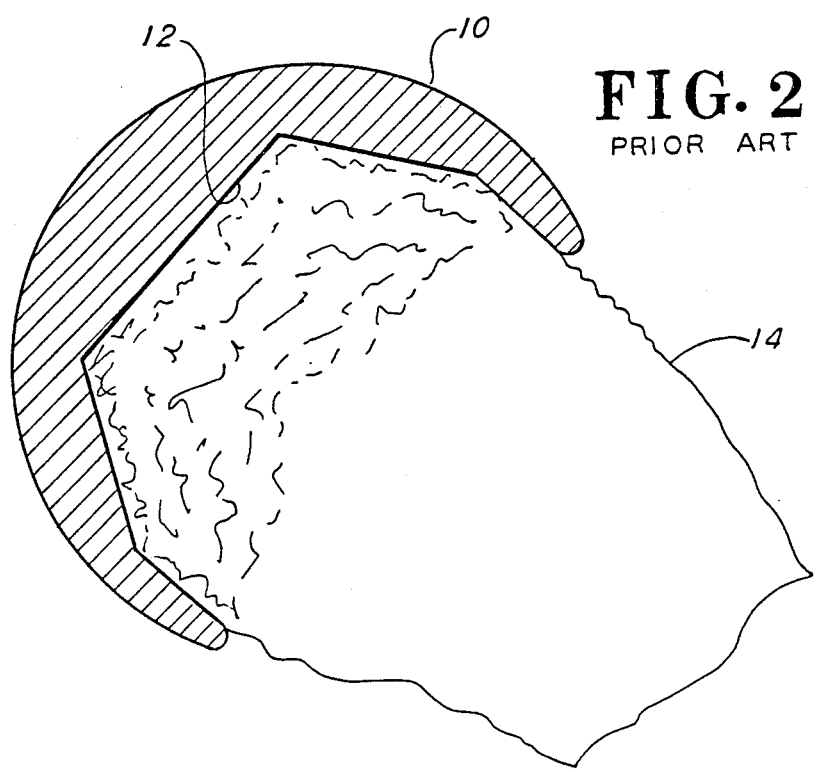

Referring now to FIGS. 3A, 3B and 3C, there is shown a hip surface replacement prosthesis 40 embodying the present invention and including a smooth, highly polished, spherical outer applied load receiving surface 42, a porous-coated interior primary surface indicated by general numerical designation 48, and a longitudinally extending stem 58 extending centrally from the interior of the prosthesis. The prosthesis 40 is for being implanted in the resected head 44 of the femur 46 with the stem 58 being driven into a prepared hole 62 formed in the neck 60 of the femur 46 and with the resected femur head 44 being prepared, in a manner known to those skilled in the prosthesis implantation art, to be complementary in shape to the interior surface of the prosthesis 40. The outer applied load receiving surface 42 of the prosthesis 40 is for replacing the articular surface of the head of the femur and for receiving the load applied to the prosthesis during articulation. The porous-coated interior surface 48 is defined by a flat central portion 52 continuing into a spherical intermediate portion 54 and continuing into a cylindrical interior surface 56; the interior surface 48 is for interlocking fixation with the femur head 44 and for providing primary transfer of the applied load to the femoral head. The porous-coated interior surface 48 provides interlocking fixation between the prosthesis 40 and the resected head of the femur by direct bone ingrowth, over a period of time, of the resected femoral head into the porous-coated interior surface 48 if cement is not used therebetween, or if cement is so used, the interior surface 48 provides the interlocking fixation with the resected femoral head 44 through the intermediate cement.

The stem 58 is provided with a smooth secondary outer surface 59 and provides secondary functions such as: alignment since the stem engages the prepared hole 62 in the femoral neck and this engagement guides the implant onto the resected femoral head thereby improving accuracy of implantation of the prosthesis; initial fixation by the stem 50 being wedged into the hole 62; secondary transfer of the applied load to the femur; and resistance against fracture of the neck 60 which fracture often occurs in the region where the femoral neck joins the head with such fracture being a common complication of hip surface replacement surgery. Since the surface 59 of the stem 58 is smooth, e.g. not porous-coated, no direct bone ingrowth will occur between the femur 46 and the stem 58 and, where cement is used therebetween, the connection between the smooth stem surface 59 and the femur will be weak due to the smoothness of the surface. Consider the load transfer by the region of the secondary stem surface 59 adjacent to the portion P2—P2 of the femoral neck downwardly of the dashed line 63 in FIG. 3C. If the region 61 is smooth load transfer to bone portion P2—P2 will be reduced. Similarly, if the entire stem is smooth stress protection in the head and neck will be further reduced and hence unlike the prior art prosthesis illustrated in FIG. 1, any tendency of the bone portion P1—P1 to resorb will be substantially reduced.

It will be understood by those skilled in the art that the teaching with regard to the identification of bone portions P1—P1 and P2—P2 with regard to FIGS. 3A, 3B and 3C is diagrammatical and that in actuality such bone portions are not specifically delineatable and that the teaching of the invention is merely by way of illustration particularly with regard to the diagrammatical, not actual, illustration of FIG. 3C.

Referring now to FIGS. 4A and 4B, there is shown a humeral surface replacement prosthesis 70 embodying the present invention and for being implanted in the head of a humerus (not shown) to replace the articular surface of the humeral head. The prosthesis 70 is provided with a smooth, highly polished spherical outer load receiving surface 72 for replacing the articular surface of the humeral head and is further provided with a porous-coated primary load transfer interior surface indicated by general numerical designation 74 defined by a flat central portion 76 continuing into a spherical portion 78 continuing into a cylindrical portion 79. Further the prosthesis 70 is provided with a stem 80 having a smooth outer surface 82 comprising the secondary surface, which outer surface 82 is smooth and non-porous coated and which stem is generally longitudinally extending from the interior of the prosthesis and perpendicular to the flat central interior surface 76. It will be understood by those skilled in the art that the humeral surface replacement prosthesis 70 is the structural and functional equivalent of the femoral surface replacement prosthesis 40 described above and that the reduction in stress shielding provided in this embodiment is accomplished in the same manner that the stress shielding reduction was provided in the femoral prosthesis 40 embodiment of FIGS. 3A, 3B, 3C.

Figure 5:
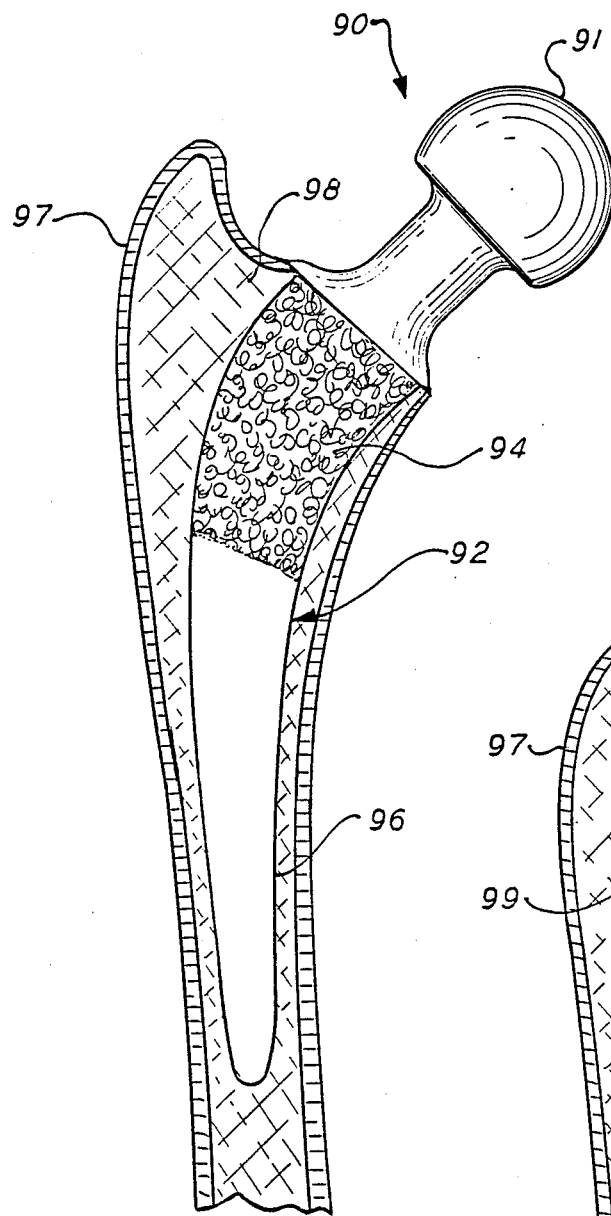
FIG. 5 is an illustration of a femoral stem prosthesis embodying the present invention and using a porous coating for direct bone ingrowth interlocking fixation.

Shown in FIG. 5 is a femoral stem prosthesis embodying the present invention and indicated by general numerical designation 90. The prosthesis includes a smooth, highly polished load receiving spherical head 91 for replacing the articular surface of the femoral head and a stem indicated by general numerical designation 92 having a porous-coated primary load transfer upper portion 94 and a smooth or non-porous coated secondary load transfer lower portion 96.

The porous-coated upper portion 94 of the stem 92 experiences direct ingrowth from the femur and hence places the prosthesis in interlocking fixation with the femur; the non-porous coated lower portion 96 of the stem 92 provides initial and secondary fixation of the prosthesis into the femur and by being smooth or non-porous coated, provides, in combination with the porous-coated upper portion 94, substantial increase in loading and reduction of stress shielding of the portion of the femur adjacent the porous-coated upper portion 94 of the prosthesis 90 in the same manner as taught above with regard to the combination of the porous-coated interior surface 48 and smooth outer surface 59 of the stem 58 of the femoral prosthesis 40.

The humeral stem prosthesis shown in FIG. 6 also embodies the present invention and is indicated by general numerical designation 100. This prosthesis is for being implanted in the head of the humerus (not shown) and is provided with a spherical head 102 at its upper portion for replacing the articular surface of the humerus with the outer surface 103 of the spherical head providing the load receiving surface for loads applied to the humerus. The humeral stem prosthesis 100 is further provided with a generally downwardly extending stem 104 for implantation in the humerus; the upper portion of the stem 105 is the primary load transfer surface and is porous-coated for either direct bone ingrowth interlocking fixation with the humerus or for use in conjunction with cement for such interlocking fixation between the prosthesis and the humerus. The lower portion 106 of the stem 104 is a smooth, e.g. non-porous-coated, secondary surface providing the above-noted secondary functions and for preventing interlocking fixation between the prosthesis and the humerus. The smooth secondary stem surface portion 106 provides the same reduction of stress shielding function as indicated above with regard to the smooth secondary surface 59 of the stem 58 of the femoral prosthesis of FIGS. 3A, 3B, and 3C.

Figure 7:
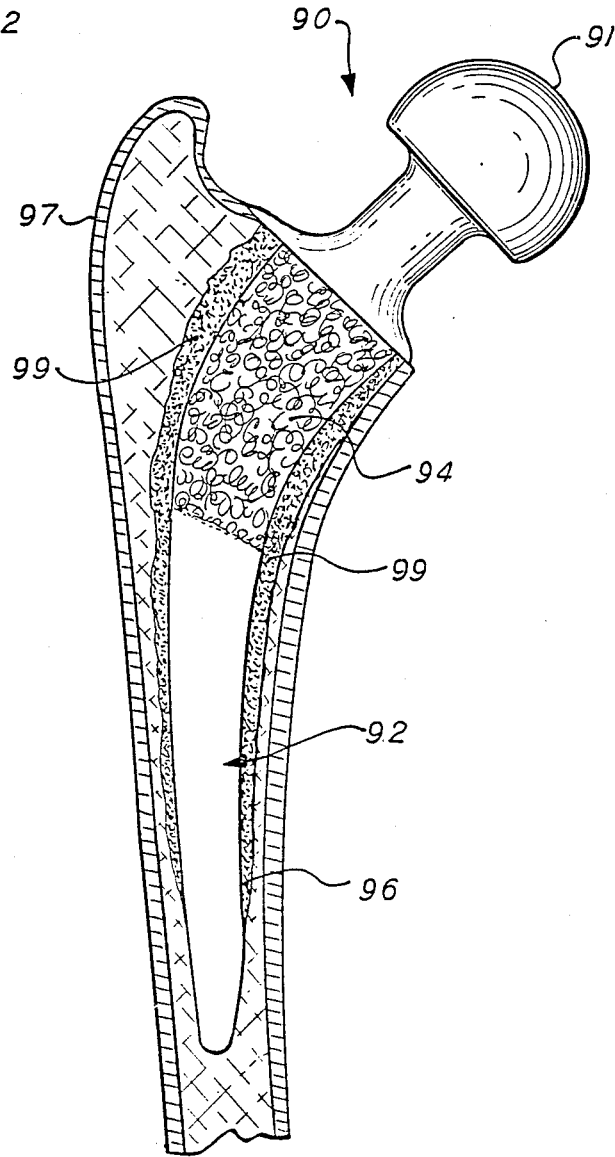
FIG. 7 is a view of a femoral stem prosthesis embodying the present invention and illustrating a porous coating for use in conjunction with cement.
Figure 9:
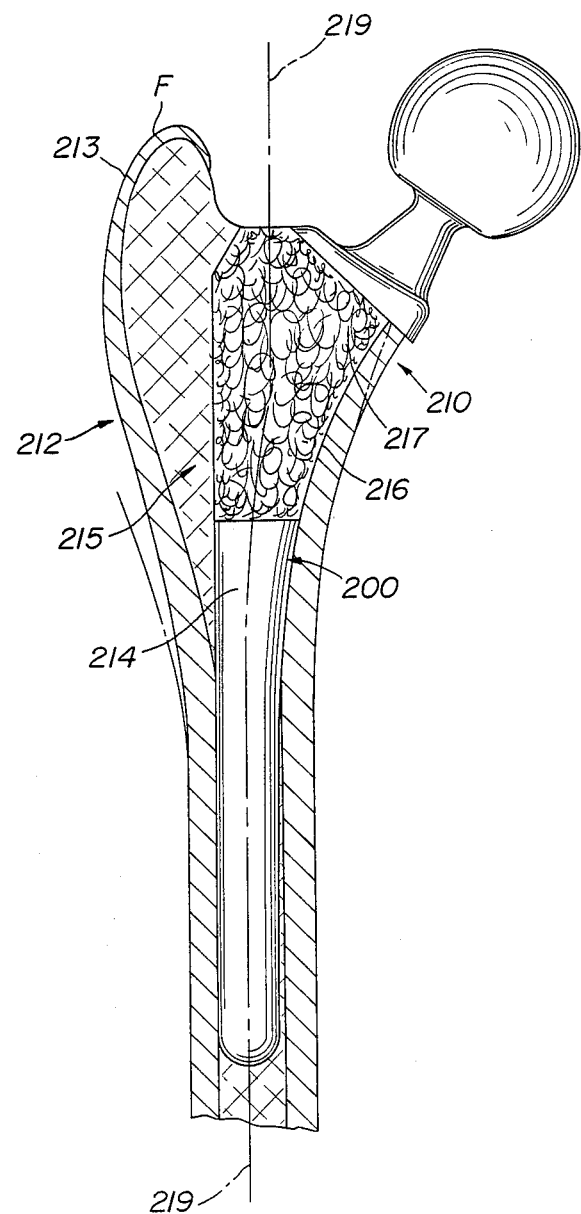

FIG. 7 shows the femoral stem prosthesis 90 of FIG. 9 wherein the porous-coated primary load transfer upper portion 94 of the stem is used not for direct bone ingrowth interlocking fixation but instead is used in conjunction with cement 99, shown on either side of the porous coating 94, for securing the prosthesis to the femur 97 thereby providing the interlocking fixation between the prosthesis and the femur. The smooth secondary femoral stem surface portion 96 provides in combination with the primary load transfer porous-coated stem surface portion 94 the same increased loading and stress shielding reduction function as described above with regard to the teachings of the embodiment of FIG. 5.

Similarly, the femoral surface replacement prosthesis shown in FIG. 8 is the same as the femoral surface replacement prosthesis 40 of FIGS. 3A, 3B and 3C but is shown in FIG. 8 for use in conjunction with cement 49 for providing the interlocking fixation between the prosthesis 40 and the femur 46; otherwise, the prosthesis 40 of FIG. 8 performs the same stress shielding reduction functions as taught above with regard to the prosthesis 40 of FIGS. 3A, 3B and 3C.

The prostheses shown may be made of Co-Cr-Mo surgical alloy or Ti-4Al-6Va alloy or commercially pure titanium. The porous coating material may or may not be the same as the substrate metal, and may be of a polymeric material or ceramic. For example, one may use Ti-4Al-6Va substrate with commercially pure titanium porous coating or one may use a Co-Cr-Mo alloy coating on a Co-Cr-Mo alloy substrate. Alternately, stainless steel substrate may be used with a bonded ultra-high molecular weight polyethylene porous surface. A further alternate is a Co-Cr-Mo alloy substrate with a porous ceramic coating. Other combinations of materials and coatings are possible and will reveal themselves to one of ordinary skill in the art.

It will be understood by those skilled in the art that the present invention may be embodied in various other prostheses other than those shown in FIGS. 3–8, for example finger, toe, an elbow prosthesis, and the preferred embodiments illustrated in the drawings are merely illustrative and not limiting of the present invention.

It has been further discovered, and in accordance with the further teachings of the present invention, that further reduction in stress shielding can be achieved by further reducing the length of porous coating on the proximal stem of a partially porous coated stem-type femoral prosthesis of the type disclosed in U.S. Pat. No. 4,406,023 issued Sept. 27, 1983 to William H. Harris and entitled STEMMED FEMORAL COMPONENT FOR THE HUMAN HIP; European Pat. No. 0038902, dated November 1981, issued to Otto Frey; and to even less than illustrated in FIG. 9 which in turn is less than shown in the Harris and Frey patents. In FIG. 9 a partially porous coated stem-type femoral prosthesis 200 is shown implanted in a resected natural femur 212 and fixtured therein by direct bone ingrowth into the partial porous coating 211 provided on the proximal portion of the anterior, posterior, lateral and medial surfaces of the prosthesis stem 214. Such additional reduction in porous coating as taught below further reduces stress shielding and also reduces the amount of bone resection required for prosthesis removal thereby permitting the amount of bone stock remaining after resection to be increased in size in turn enhancing the opportunity to implant a revision or replacement prosthesis in the resected natural femur.

Recent examination of roentgenograms (X-rays) of patients with partially porous coated stem-type femoral prostheses implanted for several years, of the type illustrated in FIG. 9 and described above, has indicated that with porous coating covering only the proximal one-third of the above-noted surfaces of the prosthesis stem although such one-third is significantly shorter than disclosed in the Harris and Frey patents, significant stress protection of the proximal calcar region, indicated by general numerical designation 210 in FIG. 9, of the natural femur 212 still occurred. In a recent case where a partially coated stem-type femoral prosthesis of this type was removed due to a trauma resulting in a femoral fracture, it was observed that bone and/or bone and tissue ingrowth had occurred over the bulk of the proximal porous coated region. Further, some resorption of the proximal portion of the femur in the calcar region, e.g. calcar region 210 of FIG. 9, was evident as a result of stress protection; additionally, it was observed that on the lateral side of the femoral stem substantial ingrowth had occurred in the porous coating provided thereon and that a trabecular bone pattern, indicated by general numerical designation 215, inclined at approximately 45° with respect to the prosthesis femoral stem axis 219, had developed apparently in order to help support the load or force applied to the greater trochanter 213 by the abductor muscles, such load or force being indicated by the alphabetical designation F in FIG. 9. It was observed that stress protection had occurred at the most proximal portion of the femoral medial calcar e.g. region 210 of FIG. 9 and to a lesser extent in the most proximal anterior portion 217 and similarly on the corresponding posterior portion (not shown). In removal of the prosthesis substantial medical calcar femoral bone had to be removed as a result of bone ingrowth into the porous coating provided on the proximal medial surface of the prosthesis. Thus, the medial proximal calcar (region 210) of the femur 212 was damaged as a result of both resorption due to stress protection and the bone resection problem of removing ingrown bone and/or tissue.

The problem associated with calcar bone destruction in prosthesis removal is addressed in the above-noted Harris patent. However, it has been found that further improvement on the disclosure of the Harris patent is possible in accordance with the following teachings of the present invention and wherein bone resorption is also further reduced. It has been discovered that in order to minimize bone resorption, it is desirable that the prosthesis produce an approximation to the normal physiological load distributed throughout the proximal femur. In the normal femur, load is transferred from the femoral head through the femoral calcar region (which includes the medial, anterior and posterior aspects of the femoral neck) to the proximal femur in a widely distributed pattern so as to distribute the load over a large region of the femoral bone until finally load is transferred to the cortical shaft of the femur. It has been discovered that if the configuration of the femoral prosthesis and porous coating allows load transfer to as much of the prosthesis collar as practical and provides for distribution of the load from the prosthesis collar-femoral calcar contact to a large portion of the proximal femur, an advance in the partially coated, stem-type femoral prosthesis art is achieved by providing a more physiological loading thereby reducing undesirable bone resorption.

The primary difficulty with femoral stem prostheses of the type disclosed in the above-noted Harris patent is that the calcar of the prosthesis collar contacts only, or substantially only the medial section of the natural femoral calcar while the natural femoral calcar extends both anteriorly and posteriorly beyond the points of contact with the collar of the prosthesis. Thus, load transfer from the prosthesis collar to the femoral calcar is not as widely distributed as it can be. Further, the porous coated configuration shown in the Harris patent, although relieving bone and tissue ingrowth medially (by not porous coating the medial surface of the prosthesis stem) and thereby removing loading of the adjacent portion of the femur and in turn reducing stress protection of the proximal femoral calcar, nevertheless includes porous coated regions having relatively long medial boundaries adjacent the anterior and posterior faces of the prosthesis stem which do allow bone and tissue ingrowth therein and therefore provide a means of distal load transfer thereby relieving the load on the more proximal aspects of the anterior and posterior portions of the femoral calcar thereby producing some stress protection of these regions; further in Harris this length of porous coating laterally approaches the femur shaft producing stress protection laterally. Thus, it has been discovered that it is desirable to produce a porous coating configuration on a stem-type femoral prosthesis which has a shorter length of coating and which allows a more gradual transition of load from the femoral calcar to the shaft of the natural femur and provides less fixation distally in the anterior, posterior, and lateral faces of the prosthesis stem.

The prosthesis disclosed in the Frey patent, as in the Harris patent, also has a relatively long length of porous coating thereby placing porous material nearby cortical bone of the shaft of the femur. As a result, although some relief of stress protection occurs as a result of lack of porous coating on the distal third of the stem, nevertheless the length of porous coating is sufficient to produce stress protection of the most proximal regions of the femur thereby producing stress resorption in this area since such porous coating length is larger than the embodiment as illustrated in FIG. 9 described earlier which did produce some proximal stress protection. Other prosthetic stems known to the art, with and without a collar, apply porous coating only to the medial and lateral faces of the stem at lengths greater than half of the total length of the stem. Such coating length again places porous coating on nearby cortical shaft of the femur and thus if as expected ingrowth occurs into the distal porous coated regions, proximal stress protection of the femur will occur. Furthermore, such designs without any lateral porous coated surface do not provide the benefits of a fixation surface for development of the compression trabeculi inclined at a 45° angle discussed earlier and thus do not exploit the advantage available by the development of this trabeculi in resisting the adduction force.

Figure 10:
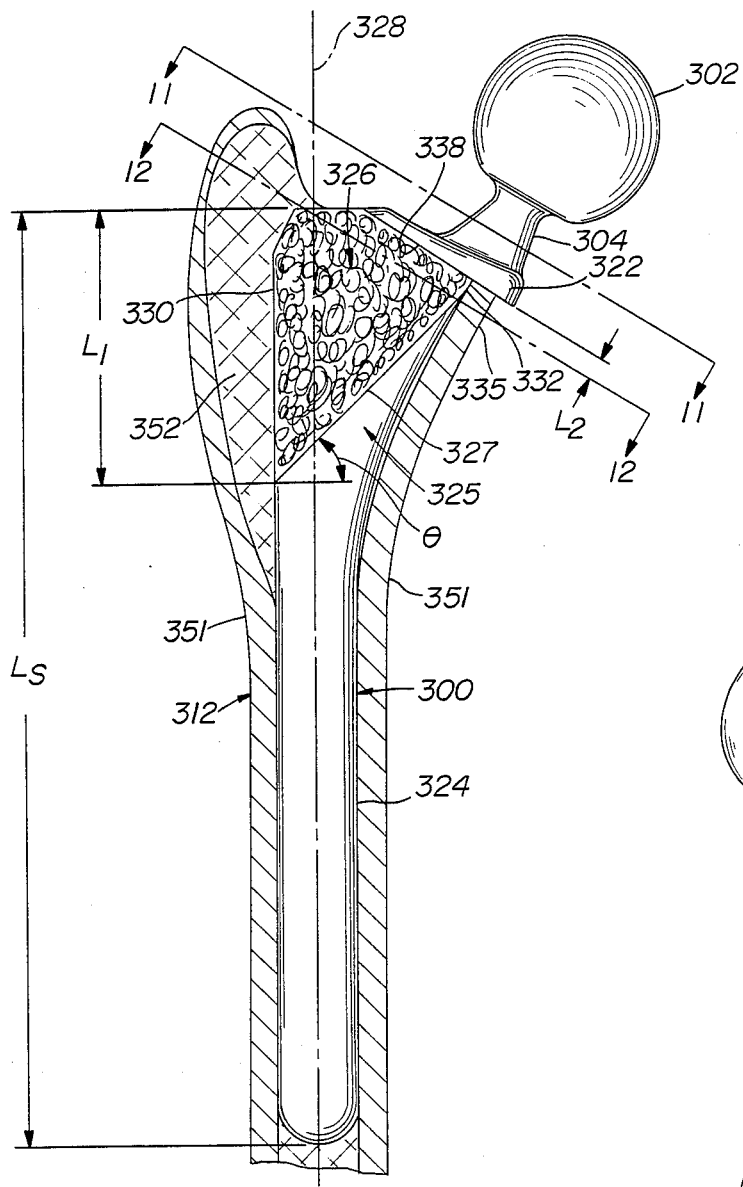
Figure 11:
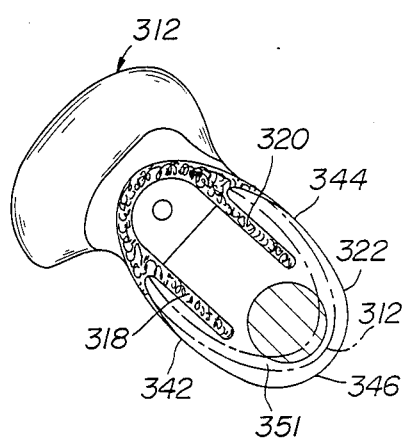
Figure 12:
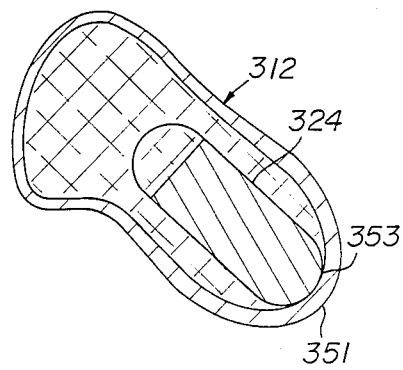

A preferred embodiment of a partially coated stem-type femoral prosthesis having an improved porous coating configuration and embodying the present invention is shown in FIGS. 10-12 and is identified by general numerical designation 300. As shown in FIG. 10, prosthesis 300 is shown implanted in the proximal end of the resected femur indicated by general numerical designation 312 and fixed therein by bone ingrowth into the porous coating configuration indicated by general numerical designation 326 and provided in accordance with the teachings of the present invention described below. The prosthesis 300 includes a spherical head 302, a neck 304, collar 322 and stem 324 having an axis 328. The collar 322 is disposed transversely on the proximal end of the stem 324, intermediate the neck and stem, and includes anterior and posterior collar portions 342 and 344 (FIG. 11) extending respectively outwardly anteriorly and posteriorly of the stem 324, the collar has a pair of access slots 318 and 320 extending generally in the lateral to medial direction, inwardly into the anterior and posterior collar portions 342 and 344, respectively, asshown in FIG. 11. As taught in detail below, access slots 318 and 320 provide access to bone resection means to facilitate resectioning of prosthesis-bone fixation interfaces between the stem 324 and a bone, such as femur 312, upon (at and/or after the prosthesis being implanted therein as illustrated in FIG. 10.

In the preferred embodiment, the anterior face indicated generally by numerical designation 325 (FIG. 10) of the proximal portion of the femoral stem 324 is provided with a porous coating as shown having a laterial boundary of length $L_1$ (measured generally along the stem axis 328), a medial boundary of length $L_2$ (measured generally along the stem axis 328) and a distal boundary 327 decreasing gradually in length from the lateral to medial direction as shown and, in the preferred embodiment, decreasing in length continuously from the lateral to medial direction and making an upwardly or superiorly extending angle $\theta$ of approximately 45° with respect to the axis 328 of the femoral stem 324; it will be understood that the posterior face (not shown) of the proximal portion of the femoral stem 324 is provided with a porous coating of the same configuration as the anterior face 325. Further, in a preferred embodiment, the lateral surface 330 and the medial surface 332 of the proximal portion of the stem 324 are porous coated only along the respective lateral length $L_1$ and medial length $L_2$; the inferior surface 338 of the collar 332 of the femoral prosthesis 300 is also porous coated in the preferred embodiment. It will be further understood that in the preferred embodiment the lateral boundaries of length $L_1$ of the porous coatings provided on the anterior and posterior faces of the proximal portion of the prosthesis stem 324 are approximately 25% of the length $L_S$ (measured generally along the stem axis 328) of the stem 324 and that the ratio of the lateral length $L_1$ to medial length $L_2$ is approximately 20:1. Further, the lateral length $L_1$ of the porous coating of the present invention is less than the prior art porous coatings, as typified by the above-noted Harris and Frey patents, whereby in accordance with the teachings of the present invention little of the porous coating is immediately adjacent to the cortical femoral bone on the lateral side of the natural femoral shaft; this reduced length $L_1$ avoids possible lateral concentrated load transfer from the femoral prosthesis stem to the lateral aspect of the natural femoral shaft thereby substantially eliminating stress protection resulting from bone ingrowth.

The configuration of the collar 322 in the preferred embodiment of the prosthesis 300 of the present invention may be further understood by reference to FIG. 11 which illustrates the contact between the collar and the underlying femur 312 the medial portion of which is shown in dashed outline in FIG. 11 where it contacts the inferior surface 338 of the collar 322. It will be noted that in this embodiment the calcar collar 322 extends anteriorly at 342 and posteriorly at 344 contacting the underlying femoral bone 312, particularly the cortical bone 351 shown by two dashed lines in FIG. 11, and in addition extends medially at 346 contacting the underlying femoral bone medially. Access slots 318 and 320, noted above, are provided in the calcar collar 322 to allow the invention of bone resectioning means for resectioning of the prosthesis-bone interfaces anteriorly, posteriorly (i.e. prosthesis-bone interfaces between the anterior and posterior faces of the stem 324 and the femur 312). It will be noted that no access to the prosthesis-bone interface is provided medially (i.e. along porous coating of length $L_2$ provided on medial face 332) since in this region there will be little bone or tissue ingrowth (due to the shortness of length $L_2$) and hence removal of the prosthesis in this region by impaction will result in minimal disruption of calcar femoral bone. And, since the collar 322 does not cover the prosthesis-bone interface between the femur and prosthesis coating of length $L_1$ provided on the lateral face 330, resection of this prosthesis bone interface can be accomplished by passing bone resection means downwardly or inferiorly along this interface.

The porous coating and prosthesis calcar collar configurations of the present invention described above and shown in the noted drawings provide an improvement over the prior art as typified by the prosthesis disclosed by the Harris patent whereby the transfer of load from the prosthesis collar to the shaft of the natural femur by means of the calcar collar can be transferred more gradually and involve more of the proximal region of the natural calcar while still reducing stress protection of the proximal femur of calcar and by reducing high stress gradient areas resulting from a sudden change in fixation support.

The porous coating configurations of the prior art stem-type femoral prosthesis, such as that disclosed in the above-noted Harris patent, is such that the length of the prior art porous coatings on the lateral, anterior and posterior faces of the prosthesis stem will place a substantial amount of porous coating adjacent to relatively stiff cortical bone. Thus, if bone ingrowth fixation occurs along this lateral anterior and posterior porous coated portions, the prosthesis will be firmly fixed at the distal portion of the porous coating to a relatively stiff cortical bone. As a result, load transfer from the head of the prosthesis will occur predominantly through the stem to the regions of distal fixation and then to the shaft of the femur. Thus, regions proximal to the distal fixation region will be stress protected to a large extent. Removal of porous coating from the medial face of the proximal portion of the femoral prosthesis, as taught in the Harris patent, although reducing stress protection to some degree will have a relatively minor role to play since there cannot be expected to be a major transfer of load by the prosthesis calcar collar of the type disclosed in the Harris patent to the proximal femoral calcar since load transfer will occur by means of the distal fixation on the lateral, anterior and posterior borders of the porous coating.

Referring further to the advantages provided by the improved prosthesis of the present invention over the prior art, particularly the prior art as typified by the porous coated stem-type femoral prosthesis disclosed in the above-noted Harris and Frey patents, and referring again to FIG. 10, since the lateral length $L_1$ of the porous coating of the present invention is significantly shorter than the prior art represented in the Harris and Frey patents, the lateral region of the porous coating of the present invention is somewhat removed from the cortical bone 351 of the natural femur 312 and is in contact with the trabecular (cancellous) bone 352 of the femur. Trabecular bone being on the order of 20 times more flexible than cortical bone, fixation by direct bone ingrowth into the porous coating 326 in this region is in a relatively flexible medium and, as such, load transfer to the cortical bone and to the femoral shaft will be much more gradual and will occur over a relatively large region of the lateral femur. Thus, fixation of the distal portion of the lateral side by bone ingrowth will not produce substantial stress protection since it will be fixed in a flexible bone and not firmly fixed to the stiff cortical bone of the femoral shaft as occurs with prior art devices of the type disclosed in the Harris and Frey patents; this is also true of the anterior face 324 and posterior face (not shown) of the prosthesis 300 embodying the present invention. From the lateral face 330 along the anterior face 325 and the posterior face (not shown), the length of the porous coating as measured along the axis 328 of the prosthesis stem 324 decreases in length (from $L_1$ to $L_2$) as it approaches the region 355 of the femoral calcar where the upper proximal portion 353 of the femoral stem 324 comes closer to stiff cortical bone 351 of the calcar region 355 of the femur 312 as illustrated in FIG. 12. Additionally, at the medial portion of the anterior and posterior faces of the proximal stem 324, the relatively short length $L_2$ of porous coating is provided in a calcar region 355 fairly nearby to cortical bone 351. Here, although the fixation by bone ingrowth into the porous coating along length $L_2$ is more firm, the length of the porous coating $L_2$ is very much less than elsewhere of the porous coating 326 and as a result there is relatively little stress protection of proximal femoral bone.

It will be understood by those skilled in the art that the porous coating configuration of the present invention avoids the distal fixation of prior art porous coatings, such as disclosed in the Harris patent, to cortical bone and instead provides a higher level distal fixation to cancellous bone in regions where the prosthesis is not immediately adjacent to stiff cortical bone thereby allowing reasonably large area of porous coating providing good attachment of trabecular (cancellous) bone to the prosthesis while still avoiding substantial stress protection. In regions medially where the prosthesis is adjacent to stiff cortical bone, the medial length $L_2$ of the porous coating of the present invention is very small avoiding substantial stress protection as a result of this reduced area of porous coating and allowing transfer of the load from the collar of the prosthesis to the natural calcar and allowing the natural calcar to transfer the load to the femoral shaft without encountering regions of porous coating fixation thereby eliminating substantial stress protection of the natural calcar.

As a result, the new and improved porous coating configuration of the present invention provides superior fixation into trabecular (cancellous) bone by allowing substantial ingrowth in regions of trabecular bone away from cortical bone while avoiding stress protection resulting from fixation to cortical bone. Such fixation to trabecular bone is also desirable in resisting shearing forces parallel to the plane of the collar-calcar contact and twisting moments about the axis of the prosthesis stem resulting from out of plane forces on the femoral head. Further maintenance of a predetermined length of coating on the lateral side allows the development of trabecular bone to help resist adduction loads by providing for a lateral surface for fixation of such bone and load transfer of this force to the lateral proximal portion of the stem.

Referring again to the calcar collar 322 of the present invention, and as shown in the preferred embodiment, the interior surface 338, as noted above, is porous coated since bone ingrowth fixation can be achieved here without providing substantial stress protection and such fixation will help resist shearing loads parallel to the surface of the collar. Further, the calcar collar 322 included in the preferred embodiment of the present invention differs from the calcar collar of the prior art, such as disclosed in the Harris patent, in that the calcar collar 322 of the present invention does extend on the anterior and posterior portions of the neck thereby providing anterior and posterior load transfer to the calcar collar thus distributing the load over a larger region of the collar and providing a more natural load transfer from the prosthesis to the natural femoral calcar.

In brief review, it will be generally understood that in accordance with the general teachings of the present invention it has been discovered by reducing the length of the partial porous coating on the proximal stem of a stem-type prosthesis to less of a length than that disclosed by the above-noted patents to Harris and Frey wherein the respective lengths of the proximal porous coatings provided on the femoral stems are approximately 40% of the length of the femoral stems as generally measured along the stem axes, reduced stress shielding can be achieved with its attendant reduced bone resorption. Still further in accordance with the general teachings of the present invention it has been discovered that by reducing the length of the partial porous coating of the type disclosed by the Harris and Frey patents to less than one-third ($\frac{1}{3}$) of the length of the stem (both as generally measured along the length of the stem axis—generally in the sense that some stems as typified by Harris and Frey are curved or have curved portions) reduced stress shielding can be achieved (note that as disclosed in FIG. 6 the length of the porous coating 105 on the proximal portion of the humeral stem 106b is approximately 30% of the length of the stem as measured generally along the stem axis). And, still further, it has been discovered that by reducing the length of such partial porous coatings on the stem of the stem-type prosthesis and by providing such partial porous coatings with the configuration disclosed in FIG. 10 and taught above, still further reduced stress shielding can be achieved with its attendant bone resorption.

In accordance with the still further teachings of the present invention, it has been discovered that the combination of the reduced (vis-a-vis the prior art) porous coating configuration 326 described above, particularly the reduced medial porous coating of length $L_2$ and the access slots 318 and 320, cooperatively permit a previously implanted stem-type femoral prosthesis having a collar (e.g. prosthesis 300) to be removed or retrieved with a greatly reduced amount of bone loss thereby greatly enhancing the probability that the remaining bone stock will be sufficient for the subsequent implantation of a replacement prosthesis.

It will be understood by those skilled in the art that many variations and modifications may be made in the present invention without departing from the spirit and the scope thereof.

We claim:

1. A prosthesis for biological fixation with a bone and implanatation therein, comprising:
   a head having a smooth generally spherical outer load receiving surface and a generally concave interior surface dimensioned for placement over the bone and said concave interior surface is provided to promote bone growth for interlocking biological fixation to the bone; and
   a stem extending from said concave interior surface of said head for implantation in said bone and for resisting fractures of said bone, said stem being smooth for substantially preventing interlocking biological fixation therewith and being tapered for driving implantation into the bone to wedge the bone against the generally concave interior surface of said head, whereby the smooth stem increases the portion of the lead applied to the concave interior surface and thereby reduces stress shielding in the interlocking biological fixation between the bone.

2. A prosthesis according to claim 1 wherein the stem extends generally centrally from said concave interior surface of said head.

3. A prosthesis as in claim 1 wherein said generally concave interior surface of said head comprises a flat central portion surrounding and adjacent said stem; a spherical concave portion adjacent said flat portion and generally concentric with said spherical exterior surface and a generally cylindrical portion substantially adjacent said spherical portion.

* * * * *